US010369252B2

(12) United States Patent
Fong et al.

(10) Patent No.: US 10,369,252 B2
(45) Date of Patent: Aug. 6, 2019

(54) ELECTROSPUN THREE-DIMENSIONAL NANOFIBROUS SCAFFOLDS WITH INTERCONNECTED AND HIERARCHICALLY STRUCTURED PORES

(71) Applicant: South Dakota Board of Regents, Pierre, SD (US)

(72) Inventors: Hao Fong, Dakota Dunes, SD (US); Tao Xu, Rapid City, SD (US); Yong Zhao, Dakota Dunes, SD (US); Todd J. Menkhaus, Dakota Dunes, SD (US)

(73) Assignee: South Dakota Board of Regents, Pierre, SD (US)

( * ) Notice: Subject to any disclaimer, the term of this patent is extended or adjusted under 35 U.S.C. 154(b) by 84 days.

(21) Appl. No.: 15/539,517

(22) PCT Filed: Dec. 23, 2015

(86) PCT No.: PCT/US2015/000507
§ 371 (c)(1),
(2) Date: Jun. 23, 2017

(87) PCT Pub. No.: WO2016/105581
PCT Pub. Date: Jun. 30, 2016

(65) Prior Publication Data
US 2018/0015201 A1    Jan. 18, 2018

Related U.S. Application Data

(60) Provisional application No. 62/095,994, filed on Dec. 23, 2014.

(51) Int. Cl.
*A61F 2/00* (2006.01)
*A61F 2/02* (2006.01)
(Continued)

(52) U.S. Cl.
CPC ........... *A61L 27/18* (2013.01); *A61L 27/3834* (2013.01); *A61L 27/50* (2013.01); *A61L 27/54* (2013.01);
(Continued)

(58) Field of Classification Search
None
See application file for complete search history.

(56) References Cited

U.S. PATENT DOCUMENTS

2002/0018797 A1   2/2002  Cui et al.
2004/0028875 A1   2/2004  Van Rijn et al.
(Continued)

FOREIGN PATENT DOCUMENTS

CN    103800097 A  *  5/2014
CN    20121457521 A    5/2014
(Continued)

OTHER PUBLICATIONS

Hiep et al. "Electro-spinning of PLGA/PCL blends for tissue engineering and their biocompatibility" J Mater Sci: Mater Med, Mar. 2010; 21(6):1969-78). (Year: 2010).*
(Continued)

*Primary Examiner* — Carlos A Azpuru
*Assistant Examiner* — Casey S Hagopian
(74) *Attorney, Agent, or Firm* — McKee, Voorhees & Sease, PLC

(57) ABSTRACT

The invention relates to electrospun three-dimensional (3D) nanofibrous scaffolds (with controllable porosities as high as about 96%) and methods of preparing the same. The electrospun 3D scaffolds possess interconnected and hierarchically structured pores with sizes ranging from tens of nanometers to hundreds of micrometers. In embodiments, the 3D scaffolds can be biocompatible and/or biodegradable. In some embodiments, the 3D scaffolds can be conductive.
(Continued)

In some embodiments, the 3D scaffolds can contain bioactive species.

11 Claims, 11 Drawing Sheets

(51) Int. Cl.

| | |
|---|---|
| D01D 5/00 | (2006.01) |
| A61L 27/18 | (2006.01) |
| A61L 27/38 | (2006.01) |
| A61L 27/50 | (2006.01) |
| A61L 27/54 | (2006.01) |
| A61L 27/56 | (2006.01) |
| D04H 1/728 | (2012.01) |
| D04H 1/4242 | (2012.01) |

(52) U.S. Cl.
CPC .............. *A61L 27/56* (2013.01); *D01D 5/003* (2013.01); *D01D 5/0092* (2013.01); *D04H 1/4242* (2013.01); *D04H 1/728* (2013.01); *A61F 2/0077* (2013.01); *A61F 2/02* (2013.01); *A61F 2002/0086* (2013.01); *A61F 2210/0004* (2013.01); *A61F 2240/001* (2013.01); *A61L 2300/64* (2013.01); *A61L 2400/12* (2013.01); *A61L 2430/02* (2013.01); *D01D 5/0007* (2013.01); *D10B 2509/00* (2013.01)

(56) References Cited

U.S. PATENT DOCUMENTS

| | | |
|---|---|---|
| 2004/0234571 A1 | 11/2004 | Jang |
| 2007/0009572 A1 | 1/2007 | Mary Chan et al. |
| 2007/0110983 A1 | 5/2007 | Jahromi |
| 2013/0183352 A1* | 7/2013 | Xie .................... A61L 27/3834 424/400 |

FOREIGN PATENT DOCUMENTS

| | | | |
|---|---|---|---|
| KR | 101313898 B1 * | 9/2013 | |
| KR | 20120044954 B1 | 9/2013 | |
| WO | 2014021954 A2 | 2/2014 | |
| WO | WO-2014021954 A2 * | 2/2014 | ........... A61L 27/042 |

OTHER PUBLICATIONS

South Dakota Board of Regents, PCT/US15100507 filed Dec. 23, 2015, Notificaiton of Transmittal of the International Search Report and the Written Opinion of the International Searching Authority, or the Declaration, dated Apr. 22, 2016.

Xu, Tao et al., "Electrospun Polycaprolactone 3D Nanofibrous Scaffold with Interconnected and Hierarchically Structured Pores for Bone Tissue Engineering", Adv. Healthcare Mater, 2015, vol. 4, pp. 2238-2246 2015.

\* cited by examiner

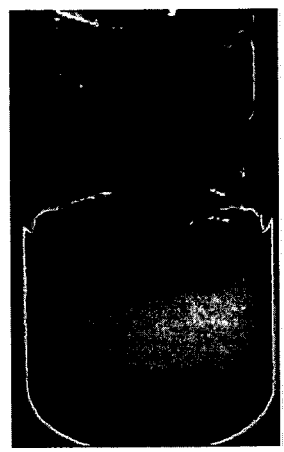 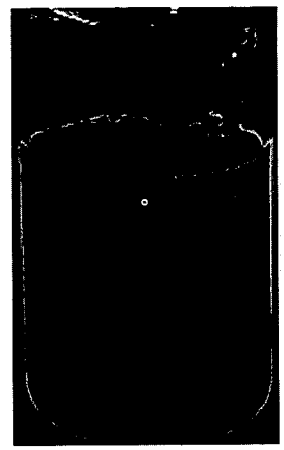 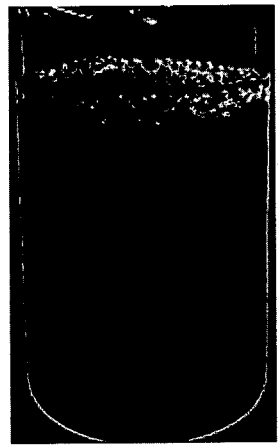
*FIG. 2A*  *FIG. 2B*  *FIG. 2C*
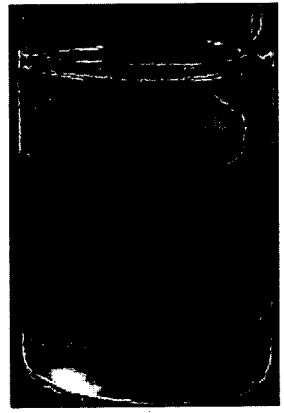 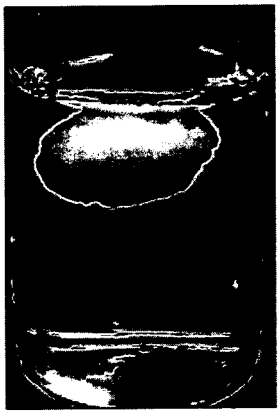 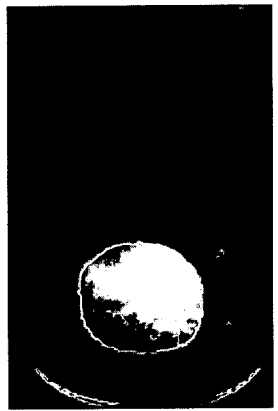
*FIG. 2D*  *FIG. 2E*  *FIG. 2F*

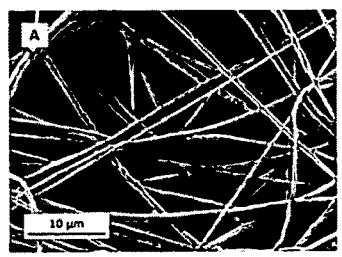 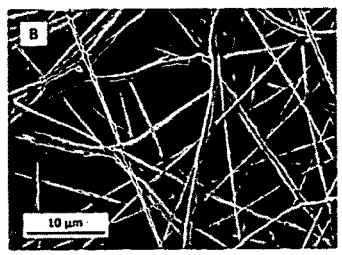 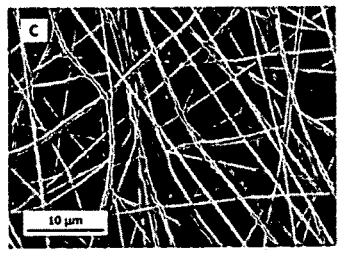
FIG. 3A　　　　　FIG. 3B　　　　　FIG. 3C
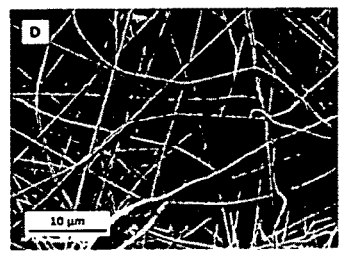 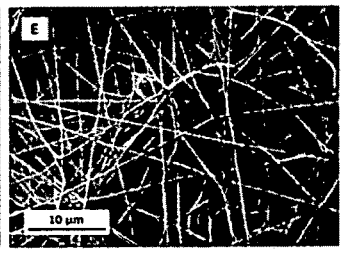 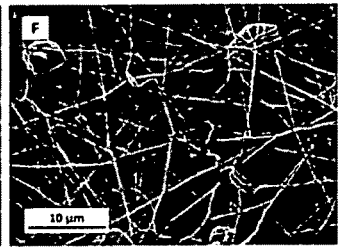
FIG. 3D　　　　　FIG. 3E　　　　　FIG. 3F

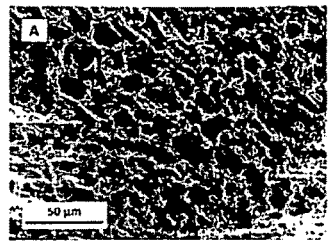 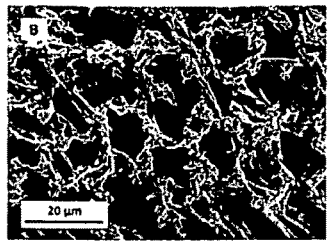 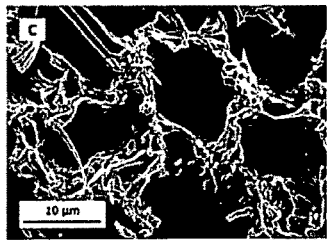
FIG. 5A　　　FIG. 5B　　　FIG. 5C
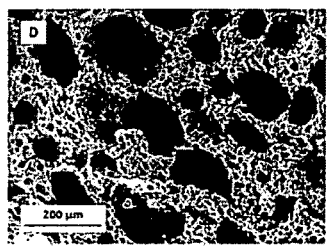 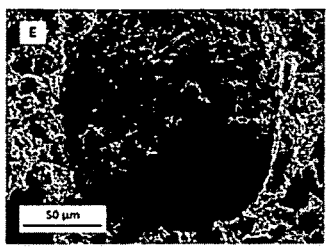 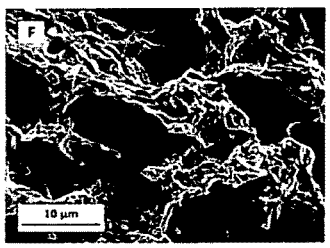
FIG. 5D　　　FIG. 5E　　　FIG. 5F
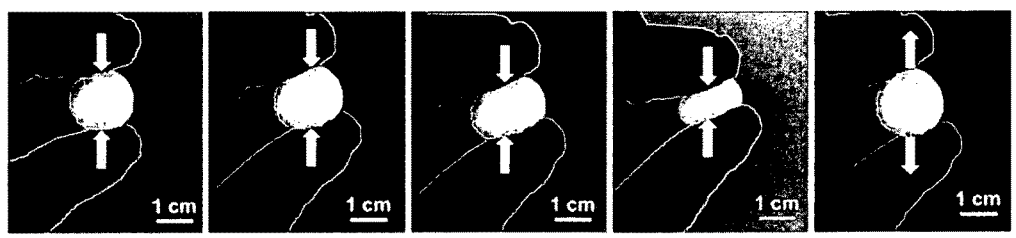
FIG. 6A　FIG. 6B　FIG. 6C　FIG. 6D　FIG. 6E

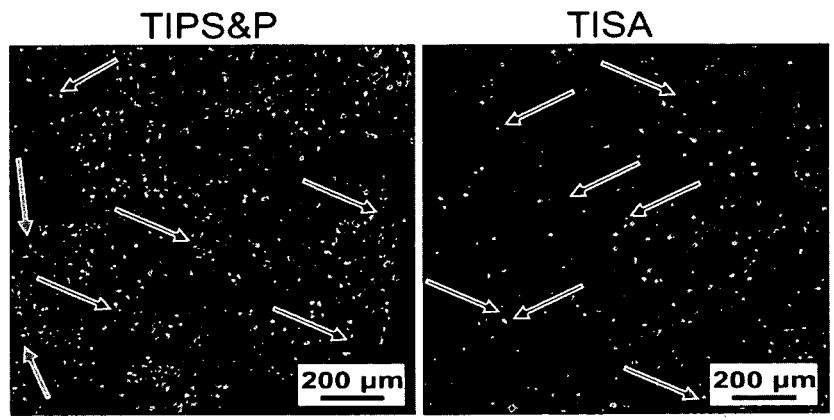
*FIG. 10A*     *FIG. 10B*
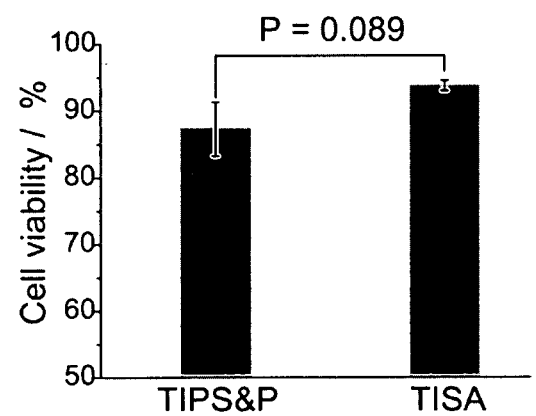
*FIG. 10C*

ELECTROSPUN THREE-DIMENSIONAL NANOFIBROUS SCAFFOLDS WITH INTERCONNECTED AND HIERARCHICALLY STRUCTURED PORES

CROSS-REFERENCE TO RELATED APPLICATIONS

This is a National Phase Application under 35 U.S.C. § 371 of PCT/US15/000507 filed on Dec. 23, 2015, which claims priority under 35 U.S.C. § 119 to provisional application U.S. Ser. No. 62/095,994 filed Dec. 23, 2014, both of which are herein incorporated by reference in their entirety.

FIELD OF THE INVENTION

This invention relates to electrospun three-dimensional (3D) nanofibrous scaffolds (with controllable porosities as high as about 96%) and their preparation methods. The electrospun 3D scaffolds possess interconnected and hierarchically structured pores with sizes ranging from tens of nanometers to hundreds of micrometers.

BACKGROUND OF THE INVENTION

Tissue engineering provides a promising approach to repair tissue and organ defects. Typically, cells are cultured into a 3D biocompatible and/or biodegradable scaffold followed by in vivo implantation. Since the scaffold acts as an artificial extracellular matrix (ECM), it would be desired to mimic critical features of natural ECMs. From the structural perspective, a natural ECM consists of interwoven protein fibers with diameters in the range from tens to hundreds of nanometers. For example, collagen, which forms fiber bundles with diameters of 50-500 nm, is the main component of natural ECMs for many tissues (e.g., skin, bone, and tendon). The nanofibrous structure of ECMs offers a network to support cells and to present an instructive background to guide cell behaviors.

The development of scaffolds that possess similar morphological structures of natural ECMs is one major challenge in tissue engineering. Presently, there are generally three methods to prepare nanofibrous scaffolds including self-assembly, phase separation, and electrospinning; however, all of the three methods have limitations. For example, the self-assembly method is difficult to control the pore size/shape inside a scaffold; and most self-assembled scaffolds are prepared in liquid environment, resulting in relatively weak mechanical properties. The phase separation method has little control over the fiber diameter/orientation in a scaffold, and the preparation time is typically very long; furthermore, such a method can only generate small pores with sizes up to about 10 μm. Although the phase separation method can be combined with the porogen leaching technique to make the needed macropores (with sizes from tens to hundreds of micrometers), such an approach is usually time-consuming and often the complete removal of porogen from a resulting scaffold is difficult.

The electrospinning method has attracted growing attentions due to its capability to make nanofibers similar to the fibrous structures in natural ECMs, and the method can be applied to a wide range of materials. Small diameters and the concomitant large surface area of electrospun nanofibers, as well as the porous structures of electrospun nanofibrous mats, can facilitate cell adhesion, proliferation, migration, and differentiation. These advantageous features make electrospun nanofibrous scaffolds well-suited for tissue engineering. However, the major limitation of electrospun scaffolds is owing to their morphological structure of overlaid nanofiber mats with apparent pore sizes in sub-micrometers; i.e., as-electrospun nanofibrous mats lack the needed macropores (with sizes from tens to hundreds of micrometers) for cell growth. Hence, it is important to develop an innovative strategy to fabricate electrospun 3D nanofibrous scaffolds with interconnected and hierarchically structured pores and high porosities; such scaffolds would better mimic natural ECMs, thereby maximizing the likelihood of long-term cell survival and the resulting generation of functional tissue in a biomimetic environment.

Several approaches have been explored recently for the fabrication of electrospun 3D nanofibrous scaffolds such as multi-layering electrospinning, electrospinning followed by various post-treatments, liquid-assisted collection, template-assisted collection, porogen-added electrospinning, and self-assembly. These approaches have proven insufficient as the scaffolds still lack desired pore structures (including size, shape, and interconnectivity of pores, as well as overall porosity of structures/scaffolds), structural flexibility, and mechanical properties.

Thus, electrospun 3D nanofibrous scaffolds and their preparation methods are still desired. It is desired that the scaffolds: (1) be highly porous to allow for cell growth and mass transport; (2) have hierarchically structured pores, so that the large pores can allow for cell penetration and the small pores can allow for mass transport; (3) have fibers with diameters in a range from tens to hundreds of nanometers; (4) possess stable shape with good mechanical properties, in particular, properties suitable for immersion in cell culture media; and (5) have the capability to form any desired shape.

Accordingly, it is an object of the invention to provide three-dimensional nanofibrous scaffolds suitable for tissue engineering and methods of preparing the same.

BRIEF SUMMARY OF THE INVENTION

The invention comprises electrospun three-dimensional (3D) nanofibrous scaffolds and methods of preparing the same. The electrospun 3D scaffolds possess interconnected and hierarchically structured pores with sizes ranging from tens of nanometers to hundreds of micrometers. The 3D scaffolds can have controllable porosities as high as about 96%. The 3D scaffolds can be prepared from biocompatible and/or biodegradable polymers such as polycaprolactone (PCL). In some embodiments, the 3D scaffolds can be conductive. In some embodiments, the 3D scaffolds can contain bioactive species.

BRIEF DESCRIPTION OF THE DRAWINGS

FIG. 2A shows short PCL nanofibers and/or tiny PCL nanofibrous mats in ethanol.

FIG. 2B shows short PCL nanofibers and/or tiny PCL nanofibrous mats in the mixture of ethanol and deionized water.

FIG. 2C shows a suspension of uniformly dispersed short PCL nanofibers and/or tiny PCL nanofibrous mats in a mixture of ethanol, water, and gelatin, where the mass ratio is about 25:24:1, respectively.

FIG. 2D shows a 3D agglomerate that was prepared by thermally induced self-agglomeration of short PCL nanofibers and/or tiny PCL nanofibrous mats.

FIG. 2E shows the PCL-based 3D agglomerate of FIG. 2D after being rinsed with distilled water.

FIG. 2F shows a PCL-based 3D nanofibrous scaffold prepared upon freeze drying.

FIGS. 3A-3F are scanning electron microscope images showing the representative morphologies of PCL nanofibers electrospun from the solutions with PCL concentrations of (A) 10 wt. %, (B) 9 wt. %, (C) 8 wt. %, (D) 7 wt. %, (E) 6 wt. %, and (F) 5 wt. %, respectively.

FIGS. 5A-5C are scanning electron microscope images showing the morphology of the inner surface of a PCL-based 3D nanofibrous scaffold prepared by the previously reported thermally induced phase separation (i.e., TIPS) method at varying magnifications.

FIGS. 5D-5F are scanning electron microscope images showing the morphology of the inner surface of a PCL-based 3D nanofibrous scaffold prepared by the previously reported thermally induced phase separation and porogen leaching (i.e., TIPS&P) methods at varying magnifications.

FIG. 6 shows a series of pictures demonstrating the mechanical elasticity of an electrospun PCL-based 3D nanofibrous scaffold prepared by the TISA method of the invention. FIG. 6A shows the original PCL scaffold. FIGS. 6B-D show a series of photographs depicting a 3D scaffold being compressed. FIG. 6E shows the scaffold with the original shape after releasing the compressing force.

FIG. 9A shows the comparison of the morphological structures prior to the seeding of cells. FIG. 9B shows low-magnification (20×) of the morphology of mouse bone marrow mesenchymal stem cells (mBMSCs) on each scaffold. FIG. 9C shows high-magnification of mBMSCs morphology on each scaffold. The cells in FIGS. 9B-9C were visualized by Texas Red-phalloidin staining (red staining appearing grey in FIGS. 9B-9C) after fixation, while the cell nucleus was mounted by DAPI (blue staining appearing white in FIGS. 9B-9C).

FIG. 10A-B show mBMSCs viability on 3D scaffolds prepared by the TIPS&P and TISA methods after 24 hours of culture. FIGS. 10A-B show the live and dead cells after 24 hours of culture. The scaffolds were both seed with 1 million cells.

FIG. 10C shows the ratio of live cells (red appearing as small white spots in greyscale, examples are indicated by arrows) to dead cells (green appearing grey in greyscale) in the 3D scaffold prepared by TIPS&P versus TISA. Data are expressed as mean±SD (n=3).

Figure 1:
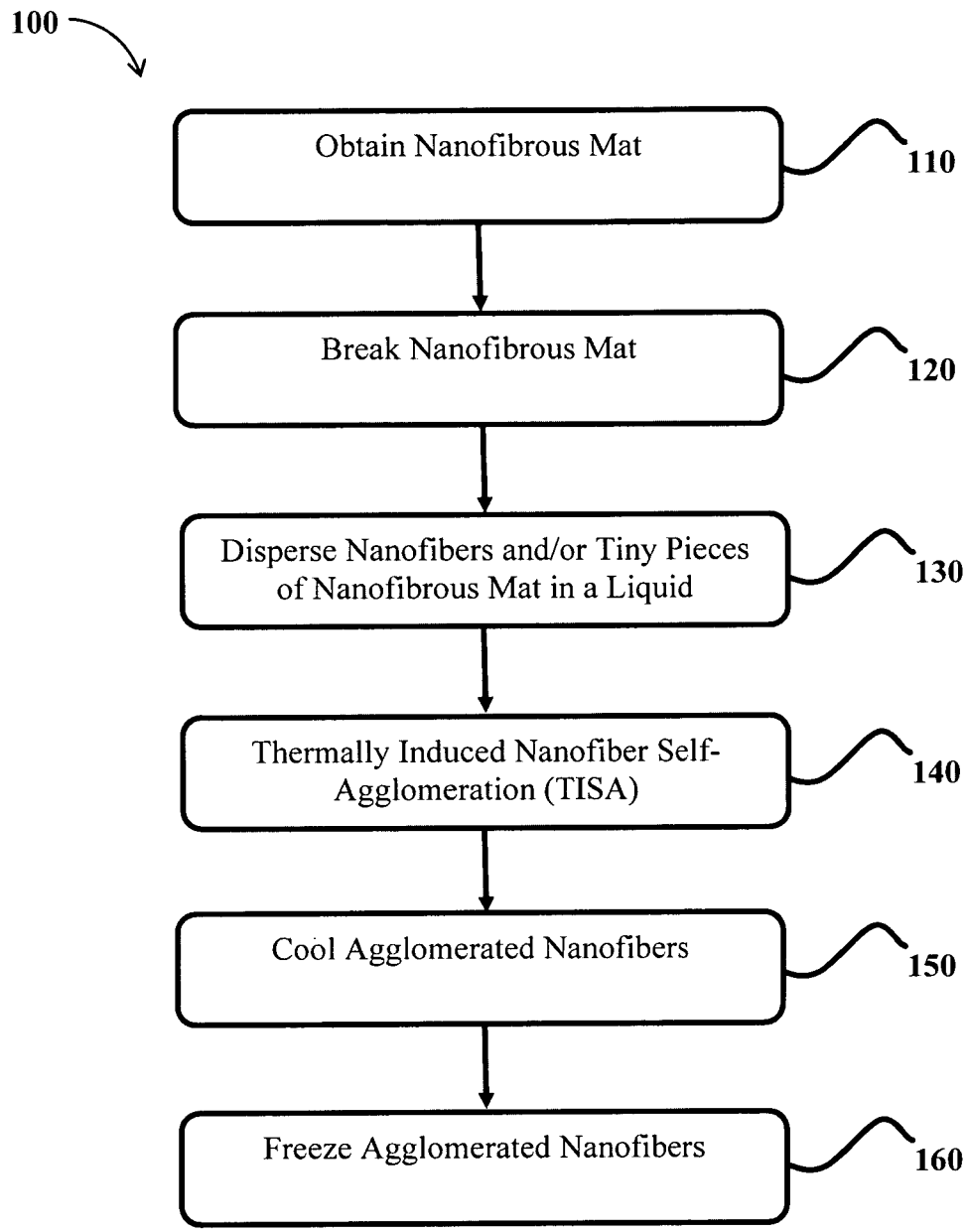
FIG. 1 shows an exemplary method of the present invention for preparing electrospun PCL-based 3D nanofibrous scaffolds.

Various embodiments of the present invention are described in detail with reference to the drawings. Reference to various embodiments does not limit the scope of the invention. Figures represented herein are not limitations to the various embodiments according to the invention and are presented for exemplary illustration of the invention.

DETAILED DESCRIPTION OF THE INVENTION

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

For example, as used in this specification and the appended claims, the singular forms "a", "an", and "the" can include plural referents unless the content clearly indicates otherwise. Furthermore, all units, prefixes, and symbols may be denoted in its International System of Units (SI) accepted form. Numeric ranges recited within the specification are inclusive of the numbers defining the range and include each integer within the defined range.

The recitation of numerical ranges by endpoints includes all numbers subsumed within that range (e.g., 1 to 5 includes 1, 1.3, 2, 2.72, 3, 3.60, 4, and 5). Thus, later recitation of more specific ranges should not be considered to be new matter.

The term "about", as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about," the claims include equivalents to the quantities. Moreover, whether or not values in the specification are modified by the term "about," the term "about" should be understood to apply to those values when desired.

The term "weight percent," "wt. %," "wt-%," "percent by weight," "% by weight," and variations thereof, as used herein, refer to the concentration of a substance as the weight of that substance divided by the total weight of the composition and multiplied by 100.

Electrospun 3D Nanofibrous Scaffolds

The compositions and methods of the present invention may comprise, consist essentially of, or consist of the components and methods of the present invention as well as other components described herein. As used herein, "consisting essentially of" means that the methods, systems, apparatuses, and compositions may include additional steps, components or ingredients, but only if the additional steps, components or ingredients do not materially alter the basic and novel characteristics of the claimed methods, systems, apparatuses, and compositions.

The 3D scaffolds with interconnected and hierarchically structured pores can be prepared by electrospinning nanofibers into randomly overlaid mat; the mat is subsequently converted into short nanofibers and/or tiny pieces of nanofibrous mat, which can then be uniformly dispersed in a liquid system. Thereafter, the system undergoes thermally induced (nanofiber) self-agglomeration (i.e., TISA) to form an agglomerate, and an electrospun 3D nanofibrous scaffold can be prepared via freeze drying of the agglomerate. In embodiments of the invention, the electrospun nanofibers can be prepared from a variety of polymers (preferably biocompatible and/or biodegradable polymers such as PCL), and the 3D scaffolds (with controllable porosities as high as about 96%) can be prepared to have different shapes (e.g., disk shape and tube shape). Embodiments of the invention can include conductive nanofibers (such as electrospun carbon nanofibers and vapor-grown carbon/graphite nanofibers), and thus the resulting 3D scaffolds possess the high electrical conductivity. The conductive nanofibers can also be prepared by coating the surface of non-conductive nanofibers with a conductive layer for making the conductive 3D scaffolds. The nanofibers can have varying diameters ranging from tens of nanometers to a few micrometers. The 3D scaffolds possess interconnected and hierarchically structured pores including macropores with sizes being hundreds of micrometers.

While electrospun 3D nanofibrous scaffolds of the invention may be ideal for tissue engineering applications, they can also be useful for any application where cell mobilization is desired, including, for example, growth of microbes such as bacteria, fungi, and viruses.

Preferably the 3D scaffolds have a porosity between about 80% and about 96%. The porosity can be tailored for the requirements of specific tissue engineering (and other) applications.

In an aspect of the invention, the electrospun 3D nanofibrous scaffolds can be prepared in many desired shapes. Preferred shapes include, but are not limited to, disks, membranes, cubes, cylinders, tubes, and spheres. The scaffold shape can be tailored for a particular tissue engineering application or to provide desired properties.

The 3D scaffolds can be prepared to possess desired properties including, biocompatibility/biodegradability, mechanical strength and elasticity, and electrical conductivity. Electrospun 3D nanofibrous scaffolds with particular properties may be prepared by the control of processing conditions and also by the selection of polymers used to make the nanofibers. For example, the electrically conductive 3D scaffolds can be prepared via incorporation of electrospun polyacrylonitrile-based carbon nanofibers.

The 3D scaffolds with particular shapes and/or electrical conductivity can provide various uses in bond regeneration, skin tissue engineering and/or wound dressing, vascular grafts, and organ implantation.

Preparation of Electrospun 3D Nanofibrous Scaffolds

The nanofibers can be prepared by electrospinning. The electrospun nanofibers can be collected by any traditional means. Preferably the nanofibers are collected in a randomly overlaid mat. The nanofibers can have varying diameters. Preferably the diameters of the nanofibers are between about 10 nm and about 2500 nm, more preferably between about 20 nm, and about 2000 nm, most preferably between about 50 nm and about 1000 nm (i.e., about 1 μm).

The polymer for preparing the nanofibers can be selected based on desired characteristics and properties. Those characteristics and properties can be influenced by the intended tissue engineering application. Preferably, the polymer is biocompatible. In some embodiments the polymer is not only biocompatible but also biodegradable. In some embodiments, electrospun carbon nanofibers (such as those made from the precursors of electrospun polyacrylonitrile nanofibers and electrospun regenerated cellulose nanofibers), vapor-grown carbon/graphite nanofibers, and non-conductive nanofibers surface-coated with a conductive layer can also be incorporated into the 3D scaffolds, since being electrically conductive can be particularly important for the growth of some cells (e.g., cardiomyocytes).

Preferred biodegradable and/or biocompatible polymers include, but are not limited to, synthetic polyesters such as polycaprolactone (PCL), polylactic acid (PLA), polyglycolic acid (PGA), poly(lactic-co-glycolic acid) (PLGA), poly(lactic acid-co-caprolactone) (PLCL), polyhydroxyalkanoate (PHA), poly(3-hydroxybutyrate-co-3-hydroxyvalerate) (PHBV), poly(ester urethane) (PEU), and their blends and/or composites, as well as natural polymers such as collagen, gelatin, regenerated silk, chitin, chitosan, cellulose, and their blends and/or composites.

Preferred conductive nanofibers include, but are not limited to, electrospun carbon nanofibers (such as those made from the precursors of electrospun polyacrylonitrile nanofibers, polyimide nanofibers, and regenerated cellulose nanofibers), vapor-grown carbon/graphite nanofibers, as well as non-conductive nanofibers surface-coated with a conductive layer.

Preferred precursors for forming conductive carbon nanofibers include, but are not limited to, polyacrylonitrile, polyimide, and regenerated cellulose.

The 3D scaffolds can be prepared to include conductive nanofibers in a number of ways. For example, two nanofibrous mats can be prepared—one that is conductive and the other not conductive. Those mats can both be broken into short nanofibers and/or tiny pieces of nanofibrous mat and then mixed together in a liquid dispersion prior to the thermally induced nanofiber self-agglomeration. Another method of preparing the 3D scaffold such that it includes conductive nanofibers is to prepare a 3D scaffold according to the TISA method of the invention followed by freeze drying and then to submerge the 3D scaffold in a liquid containing short conductive nanofibers and/or tiny pieces of a conductive nanofibrous mat so that the scaffold is attached by the conductive nanofibers and/or tiny pieces of conductive nanofibrous mat.

Preferred conductive layers for surface-coating non-conductive nanofibers include, but are not limited to, carbon/graphite layer, and any conductive layer that is biocompatible and/or biodegradable.

The electrospun nanofibers can also be functionalized by the incorporation, impregnation, and/or surface decoration of bioactive species to better control the proliferation and differentiation of cells that are seeded on the scaffolds. Such bioactive species can include, but are not limited to, enzymes, proteins (e.g., growth factors), amino acids, nucleic acids (e.g., DNAs), and drugs (e.g., antibiotics). Furthermore, for making electrospun 3D scaffolds from non-biocompatible nanofibers, such nanofibers can be surface-coated with a biocompatible layer (e.g., a gelatin layer).

During the preparation of an electrospun 3D nanofibrous scaffold, an as-electrospun nanofibrous mat can first be soaked with a liquid. Prior to soaking the nanofibrous mat, the mat can optionally cut into smaller pieces if desired. The soaked nanofibrous mat is then broken into short nanofibers and/or tiny pieces of nanofibrous mat with any suitable method. Suitable methods for breaking the nanofibrous mat into short nanofibers and/or tiny pieces of nanofibrous mat include, but are not limited to, mortar grinding and ball milling. A preferred method is by grinding the nanofibrous mat (frozen in a liquid) with a mortar. During the grinding process, the system is continuously cooled. For example, liquid nitrogen or dry ice mixed with an organic liquid (which will not dissolve the nanofibers) can be continuously added until the mat is thoroughly ground.

After a nanofibrous mat is broken, the obtained material is dispersed in a liquid and filtered to acquire short nanofibers and/or tiny pieces of nanofibrous mat capable of passing through a sieve. The desired pore size of the sieve is determined by specific application; typically, the sieve can have a pore size between about 0.5 millimeters and about 2 millimeters; preferably about 1 millimeter. Any nanofibers or portions of the nanofibrous mat left on the filter can then be returned the breaking process and further broken until they are small enough to pass through the selected sieve. This procedure can be repeated until the desired amount of short nanofibers and/or tiny pieces of nanofibrous mat are obtained.

Many liquids are suitable for the soaking, breaking, and dispersion steps, as long as the liquids do not dissolve polymer nanofibers (i.e., they are not solvents of polymers). Such liquids include, but are not limited to, organic materials/compounds (e.g., ethanol), inorganic materials/compounds (e.g., water), and their mixtures (e.g., ethanol/water mixture).

To acquire a liquid system with uniformly dispersed short nanofibers and/or tiny pieces of nanofibrous mat, the system viscosity can be optimized; furthermore, the viscosity of system can also affect the speed of subsequent thermally induced nanofiber self-agglomeration, which in turn can affect the firmness/porosity and elasticity of the resulting 3D scaffold. In some embodiments, the viscosity of the system is between about 5 cps and about 50 cps, preferably between about 10 cps and about 20 cps, and most preferably about 15 cps. In an aspect of the invention, the agglomeration can be assisted with the addition of a viscosity modifier. Preferably any viscosity modifier added is biocompatible and/or biodegradable. A preferred viscosity modifier is gelatin.

In an embodiment using PCL-based short nanofibers and/or tiny pieces of nanofibrous mat, ethanol and water as the liquid, and gelatin as the viscosity modifier, it was found that a suitable viscosity was about 15 cps, which was achieved by having ethanol, water, and gelatin in a ratio by mass of about 25/24/1.

In embodiments of the invention, the nanofiber self-agglomeration can be thermally induced. To thermally induce the self-agglomeration, the short nanofibers and/or tiny pieces of nanofibrous mat dispersed in a liquid system are heated until agglomeration is achieved. The temperature must not be so hot as to substantially vary the fiber morphology, but rather sufficient to cause self-agglomeration. In general, the temperature is about 5° C. below the melting point of polymer. For example, in an embodiment employing a PCL-based 3D nanofibrous scaffold, the temperature is preferred at about 55° C. Once the nanofibers have sufficiently agglomerated, the temperature of the system should be quickly lowered to prevent further shrinkage and/or agglomeration. For example, in an embodiment employing a PCL-based 3D nanofibrous scaffold, the temperature of the system should be quickly lowered by about 30-40° C.

During the thermally induced nanofiber self-agglomeration process, different shapes of agglomerates can be prepared. These shapes can be achieved in a number of ways, including, but not limited to, by the use of a substrate during the agglomeration step, cutting the 3D scaffold. If using a substrate during the agglomeration step, the substrate can be in any desired shape, including, for example, but not limited to, a rod, a disk, a plate, and/or a ring. For example, to allow the short nanofibers and/or tiny pieces of nanofibrous mat to agglomerate on the surface of a rod-shaped substrate followed by removal of the substrate results in tube-shaped agglomerate.

After the agglomerated nanofibers are cooled sufficiently to prohibit further shrinkage or agglomeration, they can be rinsed with distilled water to remove residual liquid and/or viscosity modifier. After the agglomerated nanofibers have been rinsed, they are soaked with water and frozen. Thereafter, the ice frozen with nanofiber agglomerate can be freeze-dried to obtain a 3D nanofibrous scaffold.

The electrospun 3D nanofibrous scaffold can be soaked in a cell culturing medium without distinguishable morphological variations. Suitable cell culturing media include, but are not limited to, Phosphate Buffered Saline (PBS), Minimum Essential Medium (MEM), and Dulbecco's Modified Eagle Medium (DMEM). Prior to freeze drying, the ice frozen with nanofiber agglomerate can be cut into a desired shape; upon freeze drying, the resultant scaffold can then be used directly for growing cells without being reshaped again.

In another aspect of the invention, the freeze-dried 3D scaffold can be re-soaked with DI water followed by being frozen and then being cut into smaller pieces; in this case, the freeze drying technique is still desired to remove the water afterwards in order to retain the 3D structure. In certain embodiments of the invention, the freeze-dried 3D scaffolds can also be cut directly by a very shape cutting utensil (such as a medical blade) without resulting in considerable distortion of 3D nanofibrous structure.

The electrospun 3D nanofibrous scaffold can be sterilized by many common methods. For example, the 3D scaffold can be sterilized with ethanol; in such a case, the sterile 3D scaffold can be further rinsed with a cell culturing medium for a few times, and then used directly without being freeze-dried again.

FIG. 1 shows an exemplary method of preparing a 3D nanofibrous scaffold 100, including a first step of obtaining a nanofibrous mat by electrospinning nanofibers 110 to form a nanofibrous mat, followed by breaking the nanofibrous mat 120 to form shortened nanofibers and/or tiny pieces of the nanofibrous mat. The shortened nanofibers and/or tiny pieces of nanofibrous mat can then be dispersed in a liquid 130. Preferably, the viscosity of the dispersion can be adjusted to obtain the desired uniformity of suspension. The suspended nanofibers and pieces of nanofibrous mat undergo thermally induced nanofiber self-agglomeration to form an agglomerate 140; upon cooling of the agglomerated nanofibers 150 followed by freezing the agglomerated nanofibers 160, the agglomerate will be turned into a 3D nanofibrous scaffold. Optionally, the nanofibrous scaffold can then be formed into a desirable shape and size.

While an understanding of the mechanism is not necessary to practice the present invention and while the present invention is not limited to any particular mechanism of action, it is contemplated that, in some embodiments, the electrospun 3D nanofibrous scaffolds can be prepared by the methods described herein, variations of the methods described herein, and in other ways ascertainable and/or known by those of skill in the art. The following are exemplary embodiments of the present invention and it should be understood that the embodiments are not exclusive and may be varied in many ways. Such variations are not to be regarded as a departure from the spirit and scope of the inventions and all of such modifications are intended to be included within the scope of the claims.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials and equipment used in the following Examples included: gelatin (G1890), polycaprolactone (PCL, $M_w$=80,000), ethanol, dichloromethane (DCM), N,N-dimethylformamide (DMF), 1,4-dioxane, hexane, paraffin (wax melting point: 53-57° C.), and poly(vinyl alcohol) (PVA, $M_w$=13,000-23,000), which are commercially-available from the Sigma-Aldrich (St. Louis, Mo.). All of the chemicals and materials were used without further purifications.

Example 1

Preparation of Electrospun PCL-Based 3D Nanofibrous Scaffold by the Thermally Induced Self-Agglomeration (TISA) Followed by Freeze Drying Methods of the Invention PCL nanofibers were prepared by electrospinning as follows. PCL (5.22 g) was dissolved in 60 g DCM/DMF ($V_{DCM}/V_{DMF}$=60/40) to prepare a solution with PCL concentration of 8 wt. %. Subsequently, the solution was filled into a 30 mL BD Luer-Lok tip plastic syringe having a stainless-steel needle with 18 gauge 90° blunt end. The electrospinning setup included a high voltage power supply (Gamma High Voltage Research, Inc., Ormond Beach, Fla.) and a laboratory-produced roller with the diameter of 25 cm. During the electrospinning process, a positive high voltage of 13 kV was applied to the metal needle, which was placed at about 25 cm away from the electrically grounded roller/collector covered with aluminum foil. The flow rate of 3.0 mL/h was maintained by using a digitally controlled syringe pump (KD Scientific Inc., Holliston, Mass.), and the rotational speed of the roller during electrospinning was set at 100 rpm. The electrospun PCL nanofibers were collected as almost randomly overlaid mat on aluminum foil, and the nanofibrous mat could be easily separated from the aluminum foil.

The obtained PCL nanofibrous mat was cut into small pieces (with length and width of about 1 cm) and then soaked with ethanol. Subsequently, the small pieces of PCL nanofibrous mat soaked with ethanol were placed into a mortar, which contained liquid nitrogen. The PCL mats frozen in ethanol were then broken into short nanofibers and/or tiny pieces of nanofibrous mat upon mechanical grinding. During the grinding process, liquid nitrogen was continuously added into the mortar until the mats were thoroughly ground. The ground PCL nanofibrous mats were then dispersed in ethanol and filtered through a sieve with pore size of about 1 mm to obtain the short nanofibers and/or tiny pieces of nanofibrous mat. The pieces of nanofibrous mat left on the filter were then placed back into the mortar for further grinding. The grinding and filtering steps were repeated several times until all of the short nanofibers and/or tiny pieces of nanofibrous mat went through the sieve and were collected.

Thereafter, the acquired short nanofibers and/or tiny pieces of nanofibrous mat (dispersed in ethanol) were transferred into a glass flask. The flask was then placed under ambient conditions for 48 h, during which time the short nanofibers and/or tiny pieces of nanofibrous mat precipitated at the bottom of the flask. Once precipitated, the ethanol at the top of the flask was carefully removed by a glass Pasteur pipette.

The acquired short nanofibers and/or tiny pieces of nanofibrous mat were dispersed in ethanol again (see FIGS. 2A-2C); subsequently, a solution of gelatin in deionized (DI) water (0.1 g/mL) was added into the suspension dropwise. To obtain a uniform dispersion with about 50 mg of PCL nanofibers and to retain a good control of self-agglomeration, the optimal volume ratio of $V_{ethanol}/V_{water}/V_{gelatin\ solution}$ was adjusted to provide uniform suspension as shown in FIGS. 2A-2C. The optimal volume ratio for this exemplary embodiment was determined to be 4/2/1 $V_{ethanol}/V_{water}/V_{gelatin\ solution}$.

The glass bottle with the obtained PCL suspension (PCL=~50 mg, $V_{ethanol}$=4 mL, $V_{water}$=2 mL, $V_{gelatin\ solution}$=1 mL) was submerged into a water bath at 55° C. for 3 min. During this time period, the PCL short nanofibers and/or tiny pieces of nanofibrous mat spontaneously agglomerated into a 3D structure, as shown in FIG. 2D. Immediately thereafter, the bottle/vial with PCL-based 3D agglomerate was placed into ice water for 30 min to prevent the further shrinkage and/or agglomeration. Finally, the obtained PCL-based 3D agglomerate was rinsed with DI water for several times to remove the ethanol and gelatin (FIG. 2E).

Prior to freeze drying, the PCL-based 3D agglomerate was soaked with DI water and placed at −15° C. for 30 min to turn the water into ice. The obtained sample was then submerged into liquid nitrogen for a few minutes. Subsequently, the sample was put into a pre-cooled glass flask followed by being freeze-dried at room temperature for 24 h. FIG. 2F depicts an exemplary electrospun PCL-based 3D nanofibrous scaffold fabricated by the thermally induced self-agglomeration (TISA) followed by freeze drying methods.

Example 2

Comparison of Electrospun PCL-Based 3D Nanofibrous Scaffold of the Invention with Three Types of Control Scaffolds For comparison, three types of control samples were prepared. The first control was 2D PCL nanofibrous mat (i.e., as-electrospun PCL nanofibrous mat). The second control was a PCL-based 3D nanofibrous scaffold prepared by the thermally induced phase separation (TIPS) method. The third control was a PCL-based 3D nanofibrous scaffold with macropores prepared by combination of the TIPS method and porogen leaching technique (TIPS&P).

Preparation of 2D PCL Nanofibrous Mats

The first type of control samples were the as-electrospun mats consisting of almost randomly overlaid PCL nanofibers; for ease of presentation, this type of control samples were denoted as ESPIN. Each control sample of this type had the thickness of about 220 μm and the mass per unit area of about 46 g/m².

Preparation of PCL-Based 3D Nanofibrous Scaffolds via TIPS Method

The second type of control samples were the PCL-based 3D nanofibrous scaffolds prepared via the TIPS method as reported in literature. In brief, a 10 wt. % PCL solution was first made by dissolving PCL in a mixture solvent of 1,4-dioxane and DI water in a mass ratio of about 90:10 at 40° C. Thereafter, 3 mL of this PCL solution was transferred into a glass vial at −15° C. for 3 h to allow for phase separation of 1,4-dioxane and DI water. This was followed by submerging the system in liquid nitrogen for 30 min to completely freeze the sample. Both the 1,4-dioxane and DI water were in solid state upon the above freezing treatment. Finally, a 3D nanofibrous scaffold was prepared upon freeze drying the sample for two days. The 3D nanofibrous scaffold had a diameter of about 2.3 cm and thickness of about 0.5 cm.

Preparation of PCL-Based 3D Nanofibrous Scaffolds via TIPS&P Method

The third type of control samples were the PCL-based 3D nanofibrous scaffolds with macropores prepared via combination of the TIPS method and porogen leaching technique (TIPS&P). At first, paraffin spheres (i.e., the porogen) with diameters in the range from about 100 μm to about 250 μm were prepared by dissolving PVA in DI water at 70° C. to form a 0.5 wt. % solution. Paraffin was then melted and added into the solution. After the mixture was vigorously stirred for 30 min, ice water was added into the system to solidify paraffin spheres. The mixture containing the dissolved PVA and the suspended paraffin spheres was then rinsed with DI water for several times to remove the PVA. After being dried at room temperature for one day, the paraffin spheres with the desired diameters of about 100 μm to about 250 μm were collected by using two sieves (one with the pore size of about 100 μm while the other one with the pore size of about 250 μm).

After that, 1.5 g paraffin spheres in a glass vial were placed in an oven at 37° C. for 20 min before being naturally cooled down to room temperature. Subsequently, 1.2 mL solution of 10 wt. % PCL in 1,4-dioxane and DI water was added dropwise into the paraffin sphere assembly; and the system was placed under ambient conditions for 3 h to allow the PCL solution to completely permeate into the paraffin sphere assembly. The system was then placed at −15° C. for 3 h and then submerged in liquid nitrogen for 30 min. After freeze drying for two days, the paraffin sphere assembly was immersed in hexane at 37° C. to dissolve the paraffin. The hexane was changed three times every day for two days. The hexane was eventually removed in a vacuum oven (27 mmHg) at room temperature. After the paraffin was dissolved and hexane was removed, the PCL-based 3D nanofibrous scaffolds were obtained with a diameter of about 2.3 cm and thickness of about 0.5 cm.

Comparison of Controls with Electrospun 3D Nanofibrous Scaffold of the Invention A Zeiss Supra 40VP field-emission scanning electron microscope (SEM) was used to characterize the morphological structures of the different samples. The thickness of electrospun nanofibrous mats was measured with the Alpha-Step D-100 profilometer (KLA-Tencor Corporation). The porosities were calculated according to the following equation:

$$P_{scaffold} = \frac{V - V_p}{V} \times 100\%$$

where $P_{scaffold}$ is the porosity of scaffold, V is the total volume of scaffold, and $V_p$ is the volume of PCL nanofibers (i.e., the mass divided by the density (1.145 g/cm³) of PCL).

To study the effect of PCL concentration on the morphology of electrospun nanofibers, the solutions with PCL concentrations of 10 wt. %, 9 wt. %, 8 wt. %, 7 wt. %, 6 wt. %, and 5 wt. % were investigated. As shown in FIGS. 3A, 3B, and 3C, when the PCL concentrations were at 10 wt. %, 9 wt. %, and 8 wt. %, the diameters of electrospun PCL nanofibers were in ranges of from about 500 nm to about 2 μm, about 200 nm to about 1.5 μm, and about 200 nm to about 1 μm, respectively; note that all of these nanofibers had smooth surface, and the mats contained few beads and/or beaded-nanofibers. Upon further decreasing the concentration of PCL to 7 wt. %, 6 wt. %, and 5 wt. % (FIGS. 3D, 3E, and 3F), beads and/or beaded-nanofibers emerged and/or became identifiable, even though the diameters of PCL nanofibers substantially decreased to about 100-700 nm, about 100-500 nm, and about 100-400 nm, respectively. Hence, the solution with PCL concentration of 8 wt. % was selected for making electrospun nanofibers in the following studies.

Figure 4A:
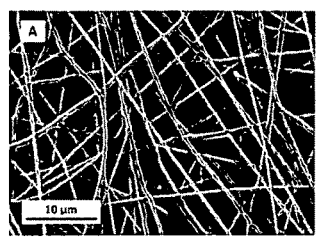
FIG. 4A is a scanning electron microscope image showing the typical morphology of an electrospun PCL nanofibrous mat.
Figure 4B:
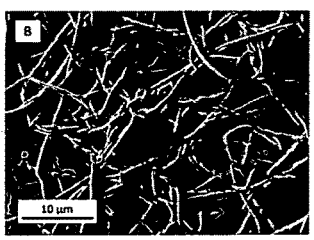
FIG. 4B is a scanning electron microscope image showing the morphology of a fragmented PCL nanofibrous mat.
Figure 4C:
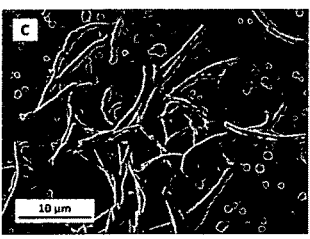
FIG. 4C is a scanning electron microscope image showing the morphology of shortened PCL nanofibers.
Figure 4D:
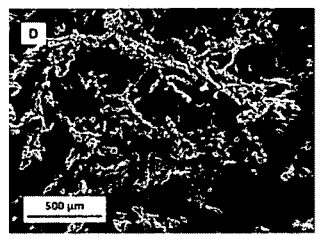
FIGS. 4D-4F are scanning electron microscope images showing the morphology of the outer surface of an electrospun PCL-based 3D nanofibrous scaffold prepared by the thermally induced (nanofiber) self-agglomeration (i.e., TISA) method of the invention at varying magnifications.
Figure 4E:
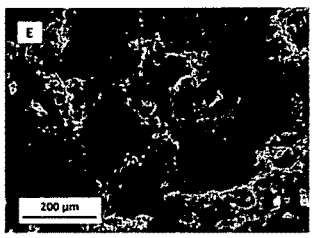
Figure 4F:
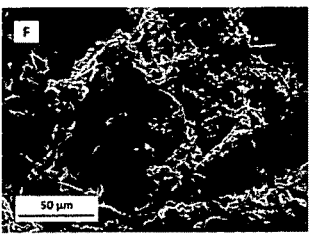
Figure 4G:
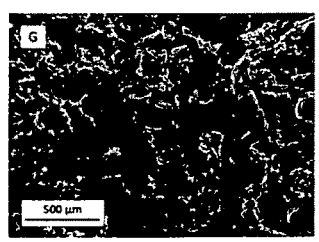
FIGS. 4G-4I are scanning electron microscope images showing the morphology of the inner surface of an electrospun PCL-based 3D nanofibrous scaffold prepared by the TISA method of the invention at varying magnifications.
Figure 4H:
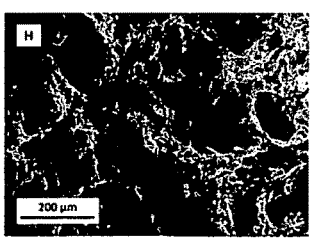
Figure 4I:
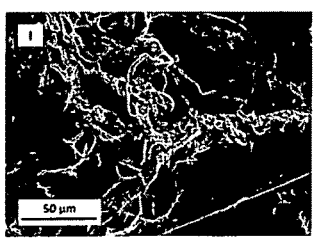

As shown in FIG. 4A, the electrospun PCL nanofibrous mat contained almost randomly overlaid nanofibers with diameters ranging from about 200 nm to about 1 μm. These nanofibers had smooth surfaces, and the mat contained almost no microscopically identifiable beads and/or beaded-nanofibers. Upon mechanical grinding in liquid nitrogen, both fragmented PCL nanofibrous mats/pieces (FIG. 4B) and shortened individual PCL nanofibers (FIG. 4C) were obtained. Note the PCL nanofibers could retain their fiber morphology after being fragmented/shortened, dispersed, and agglomerated (see FIGS. 4D-4I).

The parameters of different nanofibrous structures are summarized in Tables 1 and 2. Note that electrospun PCL-based 3D nanofibrous scaffolds (the TISA samples of the invention) had higher values of porosity and lower values of density, in comparison with other structures of the ESPIN, TIPS, and TIPS&P samples. The TISA samples had hierarchically structured pores with sizes ranging from tens of nanometers to about 300 pm, as shown in FIGS. 4D to 4I.

It is known that the porosity and pore structure of a scaffold have significant impacts on cellular migration, proliferation, differentiation, as well as tissue formation; in addition, cells and tissues could exhibit different responses to different pore sizes/structures. For example, in a scaffold with hierarchically structured pores, the macropores with sizes in hundreds of micrometers can maintain the structural stability of scaffold, support cell proliferation, ECM deposition, and tissue formation; while the pores with sizes in tens of micrometers or smaller can promote and facilitate the diffusion of nutrients and formation of vascularization. Furthermore, research endeavors have also indicated that the pores with sizes in tens of nanometers to several micrometers may have important effects on controlling some cell behaviors such as attachment/seeding and genes expressions.

The pore sizes of TIPS samples were about 10 μm, as shown in FIGS. 5A, 5B, and 5C; and the pore sizes of TIPS&P samples were in the range of about 10-250 μm, as shown in FIGS. 5D, 5E, and 5F. While for the ESPIN samples, the pore sizes were from tens of nanometers to several micrometers.

TABLE 1

Parameters of the six electrospun PCL-based 3D nanofibrous scaffold samples prepared by the TISA method of the invention

| | Sample | | | | | |
|---|---|---|---|---|---|---|
| | TISA 1 | TISA 2 | TISA 3 | TISA 4 | TISA 5 | TISA 6 |
| Diameter (cm) | 1.7 | 1.6 | 1.6 | 1.6 | 1.8 | 1.4 |
| Height (cm) | 0.6 | 0.6 | 0.5 | 0.6 | 0.5 | 0.7 |
| Volume (cm$^3$) | 1.36 | 1.21 | 1.01 | 1.21 | 1.27 | 1.08 |
| Mass (g) | 0.051 | 0.052 | 0.042 | 0.048 | 0.050 | 0.049 |
| Porosity (%) | 96.7 | 96.2 | 96.3 | 96.5 | 96.6 | 96.0 |
| Density (g/cm$^3$) | 0.037 | 0.043 | 0.042 | 0.040 | 0.039 | 0.045 |

TABLE 2

Comparisons of porosity and density of four different types of PCL-based nanofibrous structures/scaffolds (each type has six samples.)

| | | 1 | 2 | 3 | 4 | 5 | 6 | Average | Standard Deviation |
|---|---|---|---|---|---|---|---|---|---|
| Porosity (%) | ESPIN | 81.1 | 81.5 | 81.1 | 81.3 | 81.7 | 82.3 | 81.5 | 0.5 |
| | TIPS | 89.2 | 88.3 | 89.2 | 89.3 | 89.5 | 89.2 | 89.1 | 0.5 |
| | TIPS&P | 94.6 | 94.0 | 94.9 | 94.6 | 94.3 | 94.6 | 94.5 | 0.3 |
| | TISA | 96.7 | 96.2 | 96.3 | 96.5 | 96.6 | 96.0 | 96.4 | 0.3 |
| Density (g/cm$^3$) | ESPIN | 0.220 | 0.212 | 0.216 | 0.214 | 0.209 | 0.192 | 0.211 | 0.010 |
| | TIPS | 0.126 | 0.134 | 0.123 | 0.122 | 0.121 | 0.124 | 0.125 | 0.005 |
| | TIPS&P | 0.062 | 0.068 | 0.058 | 0.061 | 0.064 | 0.062 | 0.063 | 0.003 |
| | TISA | 0.037 | 0.043 | 0.042 | 0.040 | 0.039 | 0.045 | 0.041 | 0.003 |

As shown in FIG. 2G, the fragmented/shortened electrospun PCL nanofibrous mats were able to form 3D agglomerate upon being heated at 55° C.; while a 3D agglomerate could be further converted into a 3D nanofibrous scaffold upon freeze drying. The electrospun PCL nanofibers were soft as silk; intriguingly, the resulting PCL-based 3D scaffolds were elastic as sponge, as demonstrated in FIG. 6. FIG. 6A shows a PCL-based 3D nanofibrous scaffold being held between two fingers. FIGS. 6B-6D show the 3D scaffold being increasingly compressed between the fingers, with the greatest compression shown in FIG. 6D. FIG. 6E shows the 3D scaffold after releasing the scaffold from the compression. This demonstrates the elasticity of the 3D nanofibrous scaffolds.

Example 3

Optimizing the Preparation of Electrospun PCL-Based 3D Nanofibrous Scaffolds

Electrospun PCL-based 3D nanofibrous scaffolds were prepared according to the method described in Example 1, except that the use of water and gelatin was first omitted. However, it was found that if only ethanol was used as the agglomeration medium, there was not enough resistance in the suspension system during the thermal treatment; as a result, the self-agglomeration of PCL short nanofibers and/or tiny pieces of nanofibrous mat occurred too fast, and the resulting agglomerate was too firm (i.e., the porosity was too low). While not wishing to be bound by the theory, it is believed, that this was probably because the viscosity of suspension system was too low to keep the suspended PCL nanofibers steady.

Thus, it was decided to add a viscosity modifier to increase the viscosity of suspension system. Gelatin was selected due to its biological origin, biodegradability, biocompatibility, and commercial availability; while DI water was also added for improving the solubility of gelatin in the mixture system. After the gelatin and DI water were added into the system, PCL short nanofibers and/or tiny pieces of nanofibrous mat could be uniformly dispersed since the system viscosity was distinguishably higher; note that the gelatin concentration was optimized to control the speed of nanofiber self-agglomeration, the porosity, and the final shape of the PCL-based 3D nanofibrous scaffolds. The optimal mass ratio of ethanol/water/gelatin was determined to be about 25/24/1 (with a system viscosity of about 15 centipoise).

Figures 7A, 7B, 7C:
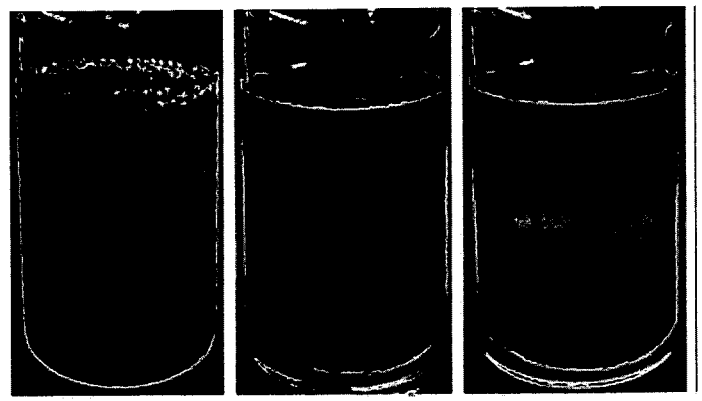
FIGS. 7A-7G show a series of pictures demonstrating the formation of PCL-based 3D nanofibrous agglomerate via the TISA method of the invention: (A) uniform suspension of short PCL nanofibers and/or tiny PCL nanofibrous mats before thermal treatment; and the suspension after being heated at 55° C. for (B) 30 seconds, (C) 60 seconds, (D) 90 seconds; (E) 120 seconds, and (F) 150 seconds, respectively; and (G) the obtained agglomerate after thermal treatment for 180 seconds.
Figures 7D, 7E, 7F, 7G:
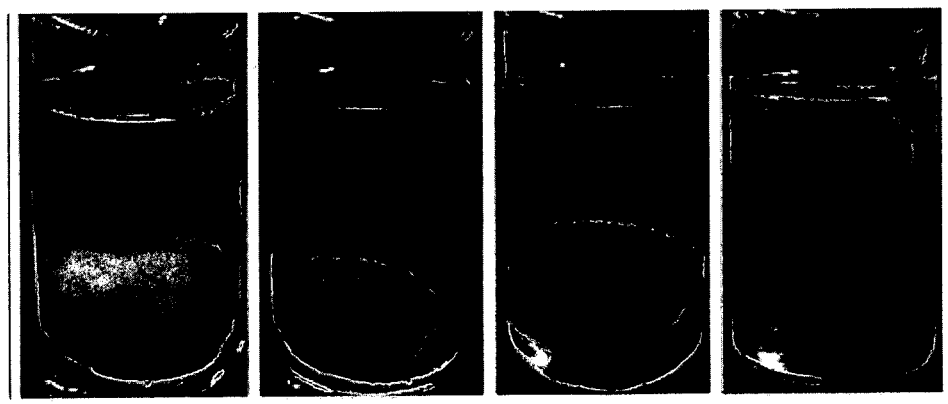

As shown in FIG. 7, the TISA process in uniform suspension was recorded by a digital camera with an interval of 30 sec. Prior to the thermal treatment (FIG. 7A), the fragmented/shortened electrospun PCL nanofibrous mats were uniformly dispersed in the suspension. Upon submerge of the glass bottle into a water bath at 55° C. for 180 sec, the PCL nanofibers gradually self-agglomerated and formed a stable 3D nanofibrous structure (FIGS. 7B-7F). This was because at 55° C., the surface of PCL nanofibers might become soft/sticky, since the melting point of PCL is around 60° C.; while for the PCL on the surface of nanofibers, the melting point might be slightly lower than 60° C. due to the size effect. Immediately afterwards, the bottle was taken out of the water bath and submerged in ice water to prevent further shrinkage and/or agglomeration (FIG. 7G).

Example 4

Figures 8A, 8B, 8C:
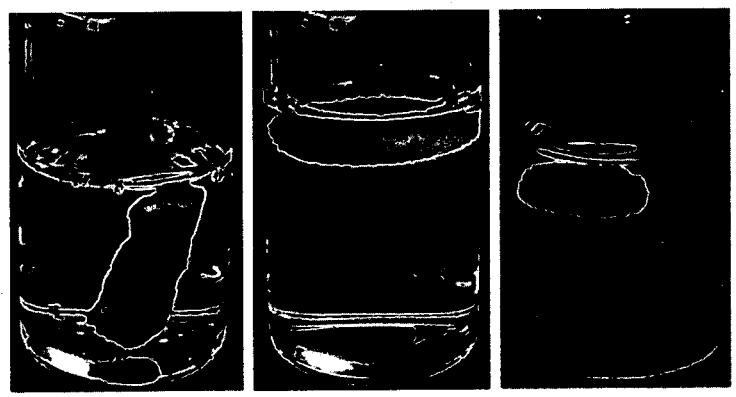
FIG. 8A shows an electrospun PCL-based 3D nanofibrous scaffold prepared by the TISA method of the invention in a tube shape.
FIG. 8B shows an electrospun PCL-based 3D nanofibrous scaffold prepared by the TISA method of the invention in a disk shape.
FIG. 8C shows a conductive 3D nanofibrous scaffold prepared by the TISA method of the invention from electrospun PCL nanofibers and electrospun polyacrylonitrile-based carbon nanofibers.

Electrospun PCL-Based 3D Nanofibrous Scaffolds with Different Shapes and the Ones with High Electrical Conductivity Electrospun PCL-based 3D nanofibrous scaffolds were made with different shapes, and some are shown in FIGS. 8A-8C.

FIG. 8A shows a tube-shaped 3D nanofibrous scaffold. It was prepared by allowing the PCL short nanofibers and/or tiny pieces of nanofibrous mat to agglomerate on the surface of a rod-shaped substrate followed by removal of the substrate. This resulted in the tube-shaped agglomerate; upon freeze drying, the tube-shaped agglomerate was converted into a tube-shaped 3D nanofibrous scaffold.

FIG. 8B shows a disk-shaped 3D nanofibrous scaffold. It was prepared using a stainless steel disk-shaped substrate during the TISA process. The short nanofibers and/or tiny pieces of nanofibrous mat agglomerated on the surface of the stainless steel disk-shaped substrate, which was then removed after agglomeration was complete. Upon freeze drying, the disk-shaped agglomerate was converted into a disk-shaped 3D nanofibrous scaffold.

FIG. 8C shows an electrically conductive 3D nanofibrous scaffold. It was prepared from PCL nanofibers together with polyacrylonitrile-based carbon nanofibers. The PCL scaffold was prepared according to the TISA and freeze drying methods of the invention. Subsequently, the acquired 3D scaffold was submerged into a liquid suspension containing polyacrylonitrile-based short carbon nanofibers and/or tiny pieces of polyacrylonitrile-based carbon nanofibrous mat. The polyacrylonitrile-based short carbon nanofibers and/or tiny pieces of polyacrylonitrile-based carbon nanofibrous mat then coated/attached on the surface of PCL nanofibers in the 3D scaffold. Note that the electrically conductive 3D nanofibrous scaffolds could also be prepared by using the mixture of PCL nanofibers and carbon nanofibers during the TISA process.

Example 5

Evaluation of Electrospun PCL 3D Nanofibrous Scaffold on Cell Morphology, Viability and Osteogenic Differentiation for Bone Tissue Engineering To study the contribution of the novel TISA scaffold on osteogenic/chondrogenic differentiation, mouse bone marrow mesenchymal stem cells (mBMSCs) were harvested and cultured from C57BJL/6 mice (5-6 weeks). Marrow content of 4 bones was plated into a 100 mm culture dish in BMSC growth medium comprised of α-MEM (Minimum Essential Medium) containing 10% fetal bovine serum (FBS) and 100 U/mL penicillin, 100 mg/mL streptomycin sulfate (Gibco). Non-adherent cells were removed while adherent BMSCs were cultured and expanded for further experiments. Primary cells prior to passage 4 were used in following experiments.

Evaluation of Cell Morphology and Cell Viability

TIPS&P and TISA scaffolds were prepared for cell seeding according to the method described in Example 1, except scaffolds were first cut into 5 mm diameter×2 mm thick discs with tissue punch; subsequently, the discs were submerged in 70% ethanol for 30 min followed by exchanging ethanol with phosphate-buffered saline (PBS) for three times (every 30 min). Scaffolds were then incubated in BMSC growth medium for 1 hour. Thereafter, the scaffolds were dried to remove residual medium by placing them between sterile gauzes. One million mBMSCs were then seeded into each scaffold by capillary action. All of the cells/scaffolds were cultured in 6-well plate with 4 mL growth medium in each well overnight and further cultured in growth or osteogenic medium up to 3 weeks on an orbital shaker in an incubator at 37° C. with 5% $CO_2$.

Visualization of mBMSCs morphologies on different scaffolds were assessed using phallacidin-FITC (Molecular Probes) and DAPI (SouthernBiotech) staining methods, which respectively labels F-actin and cell nuclear material. Cell viability on 3D scaffolds was assessed with the LIVE/DEAD cell imaging kit (Invitrogen). In brief, after culture in growth medium for 24 hours, the constructs of cells/scaffolds were placed in sterile 4-well chambered cover-glass and rinsed with Dulbecco's Phosphate Buffered Saline (DPBS). The mixed Green/Red dye was then added to stain cells; subsequently, the samples were incubated for 15 minutes at 37° C. with 5% $CO_2$. mBMSCs on four PCL nanofibrous scaffolds were imaged by a fluorescence microscope and the confocal images shown in FIGS. 9A-9C and 10A-10C.

Figure 9A:
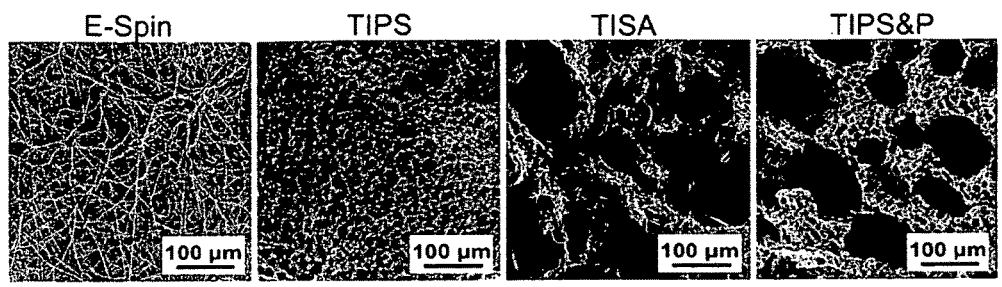
FIGS. 9A-C show a comparison of the morphologies of scaffolds prepared by ESPIN, TIPS, TISA, and TIPS&P.
Figure 9B:
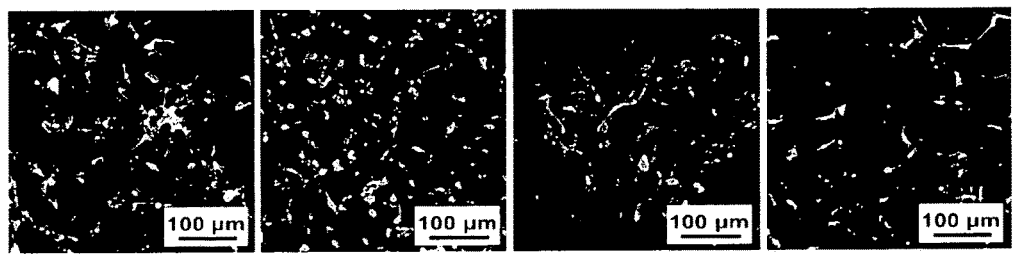
Figure 9C:
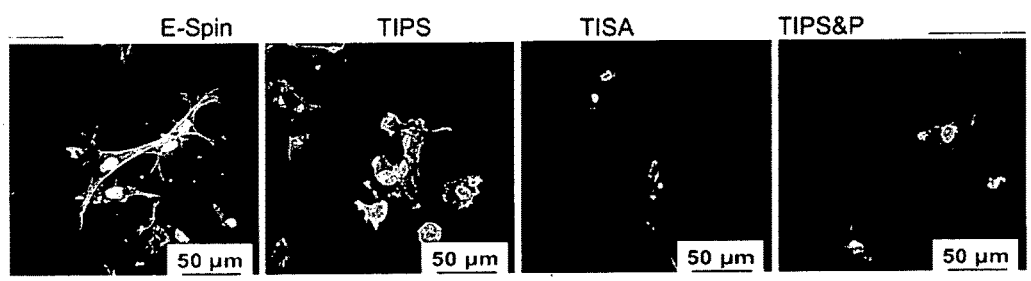

As can be seen in FIGS. 9B-9C, more cells were seen on the surfaces of 2D scaffolds (i.e., ESPIN and TIPS samples) than 3D scaffolds (i.e., TISA and TIPS&P samples). mBMSCs were able to attach and spread well on all of the four scaffolds/constructs; moreover, the cells exhibited more stretched and spindle-like shape on ESPIN scaffold, while the cells on TIPS scaffold had polygonal morphology. No distinguishable difference could be identified between the two 3D scaffolds of TISA and TIPS&P.

As shown in FIG. 10A-10C, high densities of cells were observed; and the cells were distributed throughout both 3D scaffolds. Intriguingly, the cell viability was high (~90%) on both 3D scaffolds even with such a high density of cell seeding (i.e., 1 million cells per scaffold), as evidenced by live (red appearing as small white dots in greyscale, examples indicated by arrows) and dead cells (green appearing grey in greyscale) in the images. Note that the appreciably higher viability was observed on TISA scaffold than TIPS&P scaffold (93.7% vs. 87.2%) as this might be attributed to the higher porosity of TISA scaffold. As can be seen from FIG. 10C, the cells seeded on the 3D scaffold prepared by TISA had a better ratio of live to dead cells. The ratio of live cells versus dead cells was measured by ImageJ software at low magnification (10×) from three different random areas.

Evaluation of Osteogenic Differentiation of Stem Cells In Vitro

For osteoblastic differentiation in vitro studies, mBMSCs were cultured using the methodologies described above, except osteogenic medium, α-MEM containing 10% FBS, 100 nM dexamethasone, 10 mM β-glycerophosphate, and 50 µg/mL ascorbic acid-2-phosphate (Sigma-Aldrich) was used. Mouse mesenchymal stem cell (MSC) line, C3H10T1/

2, Clone 8 (ATCC® CCL226™) was purchased from ATCC and cultured in the same BMSC growth medium as described before.

mBMSCs were cultured on TISA and TIPS&P scaffolds for up to 3 weeks in osteogenic medium. As an early osteoblastic differentiation marker, alkaline phosphatase (ALP) activity was measured after culturing for 10 days. ALP was extracted and detected with an EnzoLyte pNPP Alkaline Phosphatase Assay Kit (AnaSpec). In brief, cells on TISA scaffold or TIPS&P scaffold were homogenized in 500 µL lysis buffer provided by the kit. The lysate was then centrifuged for 15 min at 10,000 g at 4° C. and supernatant was collected for ALP assay using p-nitrophenyl phosphate (p-NPP) as a phosphatase substrate. The absorbance of the resulting supernatant was measured at 405 nm and normalized against total protein content determined by a Pierce™ BCA Protein Assay Kit. These results are shown in FIG. 11A.

As a mature mineralization marker, calcium content of each scaffold was measured by a calcium content kit after culturing for 3 weeks. The mineralization in vitro on scaffolds was examined by using the total calcium LiquiColor® kit (Stanbiolaboratory). The cell-scaffold constructs for calcium quantification were rinsed three times in DPBS (without $Ca^{2+}$ and $Mg^{2+}$) and then cut into small pieces (~1 $mm^3$) with a sharp blade. Subsequently, the chopped cell-scaffold constructs were incubated in 1 ml of 1 M hydrochloric acid for 6 h to extract calcium from ECM; thereafter, the calcium reagent working solution was added to each sample according to the manufacturer's instruction. The absorbance was measured at 550 nm, the calcium content was obtained by using the standard provided in the kit and the results represented in FIG. 11B.

Real-time PCR analysis was used to verify the expression of osteogenic genes (including Runx2 and BSP) induced by osteogenic medium at 3 weeks. Total RNA was isolated using the GeneJET™ RNA Purification Kit (Thermo Scientific™). RNA concentration was determined by absorbance at 260 nm, and an equivalent amount of RNA (0.2-1 µg) was processed to generate cDNA using the High Capacity cDNA Reverse Transcript kit (Applied Biosystems). Quantitative PCR was performed with Taqman gene expression assays (Applied Biosystems) using the Applied Biosystems 7500 Fast Real-Time PCR System (Applied Biosystems). TaqMan® Gene Expression Assays of GAPDH (Mm99999915), Runx2 (mCG122221), Sox9 (Mm 00448840), and BSP (Mm00436767) were purchased from Applied Biosystems. To further investigate the influence of scaffold on stem cells differentiation in a physiologically relevant condition, recombinant human Bone Morphogenic Protein-2 (rhBMP2, 300 ng/mL) was used instead of dexamethasone (major component of in vitro osteogenic medium) to induce a mouse MSC cell line (C3H10T1/2) for osteogenic and chondrogenic differentiations. The data from these experiments are shown in FIGS. 11C-11D.

Figure 11A:
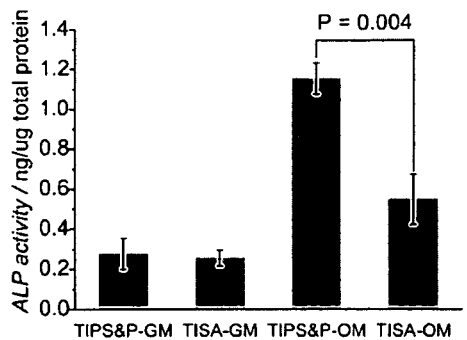
FIGS. 11A-F show mBMSCs osteogenic differentiation, and bone morphogenetic protein 2 (BMP2) induced osteogenic and chondrogenic differentiations on 3D scaffolds prepared by TIPS&P and TISA methods. Data are expressed as mean±SD (n=3).
Figure 11B:
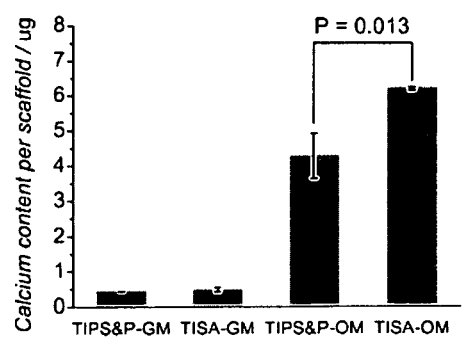
Figure 11C:
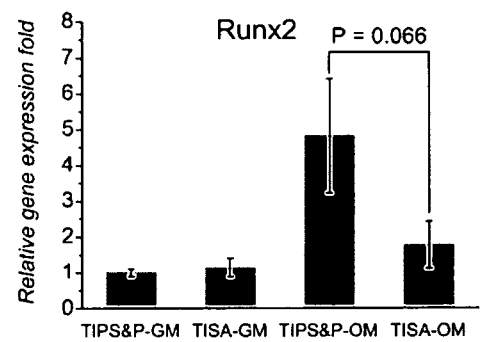
Figure 11D:
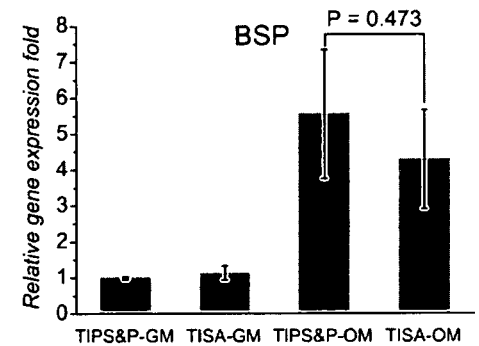

The results indicated that ALP activity levels on both 3D scaffolds were substantially elevated by osteogenic medium (compared to growth medium), while the ALP activity was higher in TIPS&P scaffold than that in TISA scaffold (FIG. 11A). Suggesting, that the stiffer TIPS&P scaffold had a higher tendency to induce early osteogenic differentiation in osteogenic medium, whereas the soft and elastic TISA scaffold was more in favor of chondrogenic differentiation even in growth medium (i.e., without BMP2 induction). Furthermore, it was evident that the calcium contents were significantly elevated on both scaffolds in osteogenic medium, whereas very small amount of calcium was identifiable in growth medium; note that the calcium content in TISA scaffold was significantly higher than that in TIPS&P scaffold (FIG. 11B).

The real-time PCR analysis results also verified that mBMSCs expressed high level of osteogenic genes (including Runx2 and BSP) induced by osteogenic medium at 3 weeks. Consistent with the ALP level, the early osteogenic marker gene Runx2 expressed at higher level on TIPS&P scaffold than that on TISA scaffold. Nevertheless, the mature osteogenic markers were similar on both TISA and TIPS&P scaffolds in osteogenic medium; and the values were significantly higher than those acquired from growth medium (FIGS. 11C-D). These results clearly demonstrated that the novel TISA scaffold was able to support mBMSC osteogenic differentiation in a comparable extent to the previously reported TIPS&P scaffold.

Figure 11E:
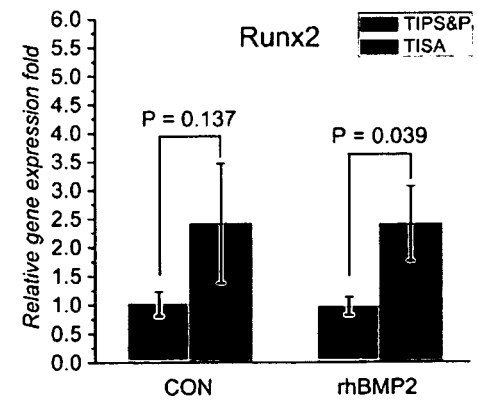
Figure 11F:
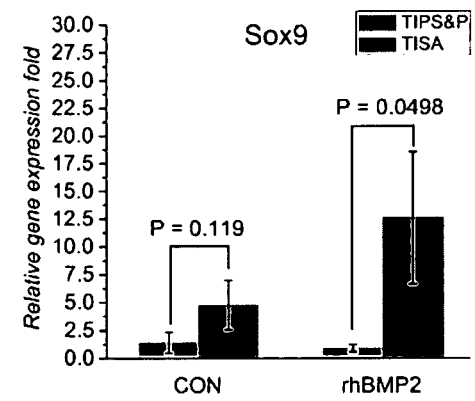
Figures 12A, 12B, 12C:
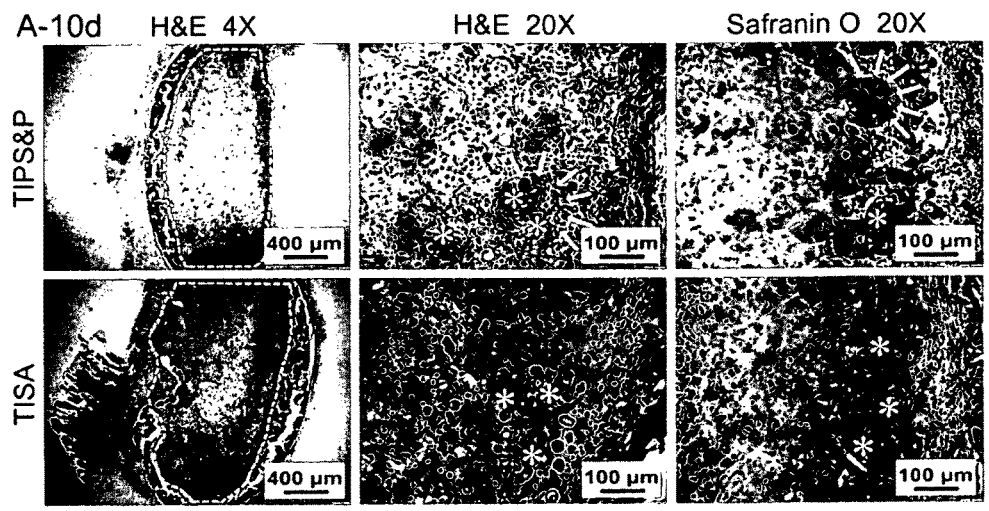
FIGS. 12A-E show BMP2-induced endochondral bone formation on 3D scaffolds prepared by the TIPS&P and TISA methods in the in vivo ectopic bone formation model.
Figures 12D, 12E:
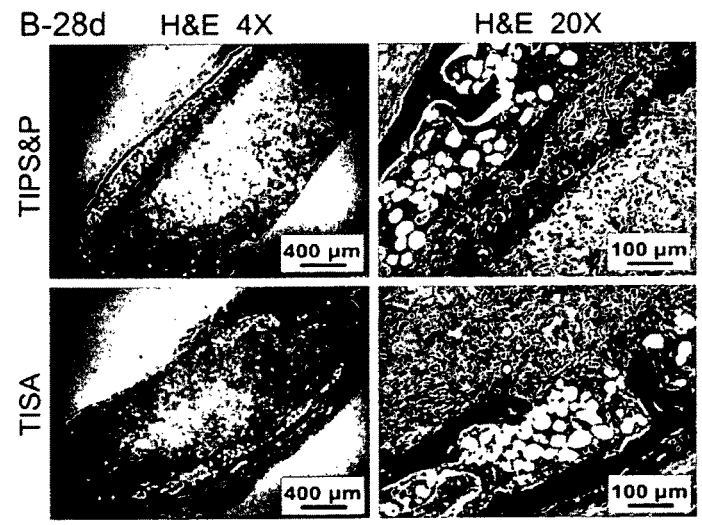

Moreover, it was observed that rhBMP2 did not distinguishably increase Runx2 expression on either scaffolds after short time (i.e., 4 days). However, stem cells expressed higher level of Runx2 on TISA scaffold than that on TIPS&P scaffold (FIG. 11E). More importantly, the expression of chondrogenic differentiation master transcription factor (i.e., Sox9) was significantly elevated on TISA scaffold even without addition of rhBMP2, while TIPS&P scaffold had negligible effects on Sox9 expression (FIG. 11F). These results suggest that the novel TISA scaffold would be more favorable for BMP2-induced osteo/chondrogenic differentiation in vitro.

Example 6

Evaluation of Electrospun PCL 3D Nanofibrous Scaffold for Bone Tissue Engineering In Vivo In addition to in vitro study, the BMP2 expressing cells were incorporated into 3D scaffolds and subcutaneously transplanted into mice for the endochondral bone formation study. In detail, C3H10T1/2 cells were transfected with adenovirus, Ad-BMP2 at 500 multiplicity of infection (MOI) one day prior to implantation. One million cells/Ad-BMP2 were then seeded on each scaffold of TIPS&P or TISA. Inbred C57BJL/6 male mice (5-6 weeks) were adopted for this study. The mice were shaved and antiseptic solution (chlorhexidine) was applied to the surgical area. Two mid longitudinal skin incisions of ~1 cm in length were made on the dorsal surface of each mouse, and 3 subcutaneous pockets were formed by blunt dissection. One scaffold was implanted subcutaneously into each pocket. Each animal received 3 cell-scaffold constructs. After placement of constructs, the incisions were closed with staples. Four mice (n=4) were euthanized at 10 and 28 days after surgery, respectively. Retrieved ossicles were fixed in 10% neutral buffered formalin for 2 days and then transferred to 70% ethanol until further analysis.

Figure 13:
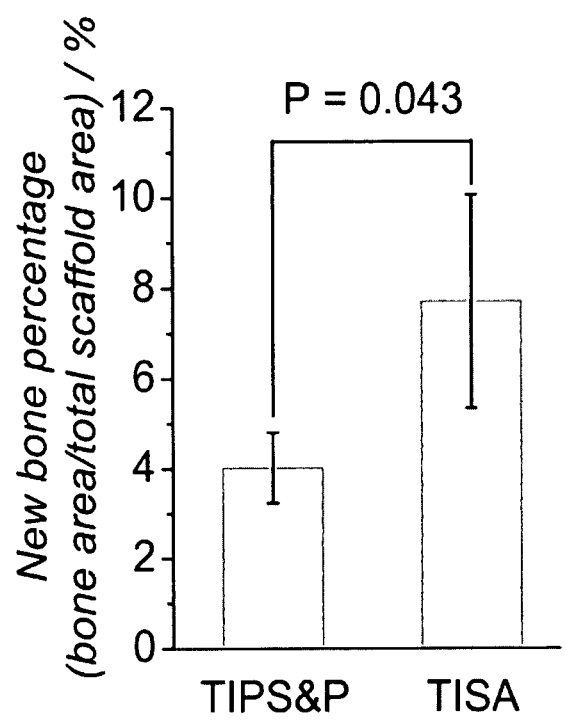
FIG. 13 shows a comparison of new bone percentages for the scaffolds prepared by TIPS&P and ISA methods.

Histological analysis was performed by taking the 28-day ossicles and subsequently decalcifying them with 15% EDTA (pH=7.2) solution for 1 day. Next, the ossicles were embedded in paraffin, whereas no decalcification was undergone for 10-day samples prior to paraffin embedding. Ten micron cross-sections were cut from the middle of scaffolds and stained with Hematoxylin and Eosin (H&E) or Safranin O for microscopic observation. The percentage of new bone area of each specimen was measured and shown in FIG. 13.

The H&E staining of 10-day samples showed that endogenous tissues (including cells and blood vessels) almost completely occupied both 3D scaffolds of TIPS&P and TISA (FIGS. 12A-E), while few tissues could be observed inside the scaffolds without macropores such as TIPS scaffold (results not shown). This confirmed that the TISA scaffold with interconnected macropores would be suitable for tissue growth in vivo, and the cells could infiltrate throughout TISA scaffold at 10 days after implantation. The BMP2 expressed by the transplanted cells induced significant cartilage-like tissue formation on both scaffolds after 10 days. As shown in FIGS. 12A-E, hypertrophic chondrocytes were found not only in superficial layer but also in deeper layers of 3D scaffolds, as identified by cartilage matrix specific Safranin O staining (red). Although no appreciable differences were identified in 10-day samples, significantly more new bone was formed on TISA scaffold (compared to TIPS&P scaffold) at 28 days measured by bone area in each slide. Most of the newly formed bone and marrow was found in the surrounding area of both 3D scaffolds, although some immature bone and/or hypertrophic cartilage matrices were found inside the scaffolds. Hence, the in vivo results demonstrated that novel TISA scaffold with interconnected macropores would act as favorable synthetic ECM for the BMP2-induced endochondral bone formation. New bone area and percentage on each slide (cover almost entire scaffold area) were measured by ImageJ software at low magnification (4×). Data are expressed as mean±SD (n=4).

The invention being thus described, it will be obvious that the same may be varied in many ways. Such variations are not to be regarded as a departure from the spirit and scope of the inventions and all such modifications are intended to be included within the scope of the following claims.

What is claimed is:

1. A method for preparing a three-dimensional nanofibrous scaffold comprising:
    forming a three-dimensional nanofibrous agglomerate by thermally induced nanofiber self-agglomeration; and
    freeze-drying the three-dimensional agglomerate to obtain a three-dimensional nanofibrous scaffold.

2. The method of claim 1, wherein said thermally induced nanofiber self-agglomeration is performed by steps comprising:
    obtaining a nanofibrous mat;
    grinding the nanofibrous mat to provide nanofibers and/or pieces of nanofibrous mat;
    filtering the nanofibers and/or pieces of nanofibrous mat through a sieve having a pore size of about 0.5 mm to about 2 mm;
    dispersing the filtered nanofibers and/or pieces of nanofibrous mat into a liquid system;
    heating the liquid system at a temperature below the melting point of polymer to allow for nanofiber self-agglomeration to form a three-dimensional agglomerate;
    cooling the liquid system to stop the self-agglomeration.

3. The method of claim 2, wherein the nanofibrous mat is obtained by electrospinning a polymer to form a nanofibrous mat.

4. The method of claim 3, wherein the polymer is biocompatible and/or biodegradable.

5. The method of claim 3, wherein the polymer is selected from the group consisting of polycaprolactone, polylactic acid, polyglycolic acid, poly(lactic-co-glycolic acid), poly(lactic acid-co-caprolactone), polyhydroxyalkanoate, poly(3-hydroxybutyrate-co-3-hydroxyvalerate, poly(ester urethane), collagen, gelatin, regenerated silk, chitin, chitosan, cellulose, and their blends and/or composites.

6. The method of claim 3, further comprising the addition of a viscosity modifier after the filtering step and before the heating step.

7. The method of claim 1, wherein the three-dimensional scaffold is electrically conductive and further comprises conductive nanofibers comprising electrospun carbon nanofibers, vapor-grown carbon/graphite nanofibers, and/or non-conductive nanofibers surface-coated with a conductive layer.

8. The method of claim 6, wherein the liquid system has a viscosity between about 5 cps and about 50 cps.

9. The method of claim 1, wherein a substrate is added to the liquid system for controlling the shape of agglomerate prior to heating, and wherein the nanofibers and/or pieces of nanofibrous mat agglomerate on the surface of the substrate.

10. The method of claim 1, further comprising sterilizing the three-dimensional nanofibrous scaffold and/or rinsing the three-dimensional nanofibrous scaffold with a cell culturing medium.

11. The method of claim 4, wherein the three-dimensional nanofibrous scaffold comprises one or more bioactive species.

* * * * *